United States Patent
Nye et al.

(10) Patent No.: US 12,014,814 B2
(45) Date of Patent: Jun. 18, 2024

(54) METHODS AND SYSTEMS FOR TUNING A STATIC MODEL

(71) Applicant: GE Precision Healthcare LLC, Milwaukee, WI (US)

(72) Inventors: Katelyn Nye, Glendale, WI (US); Gopal Avinash, San Ramon, CA (US); Pal Tegzes, Budapest (HU); Gireesha Rao, Pewaukee, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 1055 days.

(21) Appl. No.: 16/775,180

(22) Filed: Jan. 28, 2020

(65) Prior Publication Data

US 2021/0232967 A1    Jul. 29, 2021

(51) Int. Cl.
| | |
|---|---|
| *G16H 30/40* | (2018.01) |
| *G06F 18/20* | (2023.01) |
| *G06F 18/21* | (2023.01) |
| *G06F 18/40* | (2023.01) |
| *G06N 5/02* | (2023.01) |
| *G06N 20/00* | (2019.01) |

(Continued)

(52) U.S. Cl.
CPC .......... *G16H 30/40* (2018.01); *G06F 18/217* (2023.01); *G06F 18/285* (2023.01); *G06F 18/40* (2023.01); *G06N 5/02* (2013.01); *G06N 20/00* (2019.01); *G06T 7/0012* (2013.01); *G16H 50/50* (2018.01); *G06T 2207/10116* (2013.01); *G06V 2201/03* (2022.01)

(58) Field of Classification Search
CPC ........ G16H 30/40; G16H 50/50; G06N 20/00; G06N 5/02; G06F 18/217; G06F 18/285; G06F 18/40; G06T 7/0012; G06T 2207/10116; G06V 2201/03

USPC .......................................................... 706/14
See application file for complete search history.

(56) References Cited

U.S. PATENT DOCUMENTS

| | | | |
|---|---|---|---|
| 2007/0055153 A1 | 3/2007 | Simopoulos | |
| 2018/0341752 A1* | 11/2018 | Bernard | A61B 6/463 |
| 2019/0150857 A1* | 5/2019 | Nye | A61B 6/037 |

OTHER PUBLICATIONS

Prieto ("Image Retake Analysis in Digital Radiography Using DICOM Header Information", Journal of Digital Imaging 2009) (Year: 2009).*

(Continued)

*Primary Examiner* — Mark Roz
(74) *Attorney, Agent, or Firm* — McCoy Russell LLP

(57) ABSTRACT

Methods and systems are provided for tuning a static model with multiple operating points to adjust model performance without retraining the model or triggering a new regulatory clearance. In one embodiment, a method comprises, responsive to a request to tune a model, obtaining a tuning dataset including a set of medical images, executing the model using the set of medical images as input to generate model tuning output, and determining, for each operating point of a set of operating points, a set of tuning metric values based on the tuning dataset and the model tuning output relative to each operating point. An operating point from the set of operating points may be selected based on each set of tuning metric values and, upon a request to analyze a subsequent medical image, a representation of a finding output from the static model executed at the selected operating point.

19 Claims, 10 Drawing Sheets

(51) Int. Cl.
*G06T 7/00* (2017.01)
*G16H 50/50* (2018.01)

(56) References Cited

OTHER PUBLICATIONS

IRay ("iRay A6 Hand-Held Digital X-Ray System", lionsdentalsupply.com available 2016) (Year: 2016).*
Rincker ("Vision Standards Make the Cut for Medical Imaging", Medical Design Briefs 2014) (Year: 2014).*
StackOverflow "Find maximum value of a column and return the corresponding row values using Pandas" (Year: 2013).*
Python Tutorial "Tkinter dropdown example" (Year: 2019).*
Anonymous: "Revisions on how to determine the optimal threshold for a classifier and generate ROC curve?—Cross Validated", Nov. 10, 2014 (Nov. 10, 2014), XP055805906, Retrieved from the Internet: URL:https://stats.stackexchange.com/posts/ 123159/ revisions [retrieved on May 19, 2021] * pp. 2-3 *.
EP patent application 21151241.3 filed Jan. 12, 2021—Extended Search Report dated May 31, 2021; 13 pages.
Will Koehrsen: "Beyond Accuracy: Precision and Recall by Will Koehrsen : Towards Data Science", Mar. 3, 2018 (Mar. 3, 2018), XP055805901, Retrieved from the Internet: URL:https:// towardsdatascience.com/beyond-accuracy-precision-and-recall-3da06bea9f6c [retrieved on May 19, 2021] * section Example Application; pp. 10-11 *.

* cited by examiner

FIG. 3B

Table 350 — Tuning metric vs Operating Point Thresholds (10 to 99)

| | 10 | 20 | 30 | 40 | ... | 80 | 90 | 99 |
|---|---|---|---|---|---|---|---|---|
| TP | 174 | 170 | 168 | 164 | ... | 143 | 134 | 99 |
| FP | 104 | 82 | 72 | 55 | ... | 23 | 17 | 5 |
| TN | 144 | 166 | 176 | 193 | ... | 225 | 231 | 243 |
| FN | 4 | 8 | 10 | 14 | ... | 35 | 44 | 79 |
| Sensitivity | 97.8% | 95.5% | 94.4% | 92.1% | ... | 80.3% | 75.3% | 55.6% |
| Specificity | 58.1% | 66.9% | 71.0% | 77.8% | ... | 90.7% | 93.1% | 98.0% |
| PPV | 62.6% | 67.5% | 70.0% | 74.9% | ... | 86.1% | 88.7% | 95.2% |
| NPV | 97.3% | 95.4% | 94.6% | 93.2% | ... | 86.5% | 84.0% | 75.5% |
| Accuracy | 74.6% | 78.9% | 80.8% | 83.8% | ... | 86.4% | 85.7% | 80.3% |
| Balanced Acc. | 77.9% | 81.2% | 82.7% | 85.0% | ... | 85.5% | 84.2% | 76.8% |

METHODS AND SYSTEMS FOR TUNING A STATIC MODEL

FIELD

Embodiments of the subject matter disclosed herein relate to a method for tuning a static model.

BACKGROUND

Radiological medical imaging systems are often used to monitor, image, and diagnose a subject. To increase the efficacy of such systems, the use of artificial intelligence models to automatically identify and characterize radiological images is becoming more widespread.

BRIEF DESCRIPTION

In one embodiment, a method, responsive to a request to tune a static model, comprises: obtaining a tuning dataset including a set of medical images; executing the diagnostic model using the set of medical images as input to generate a model output; determining, for each operating point of a set of operating points, a set of tuning metric values based on the tuning dataset and the model output relative to each operating point; selecting an operating point from the set of operating points based on each set of tuning metric values; and, upon a request to analyze a subsequent medical image, outputting a representation of an output of the static model executed at the selected operating point.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIGS. 3A and 3B show non-limiting examples of data matrices that may be generated using the method presented in FIG. 2;

DETAILED DESCRIPTION

Figure 1:
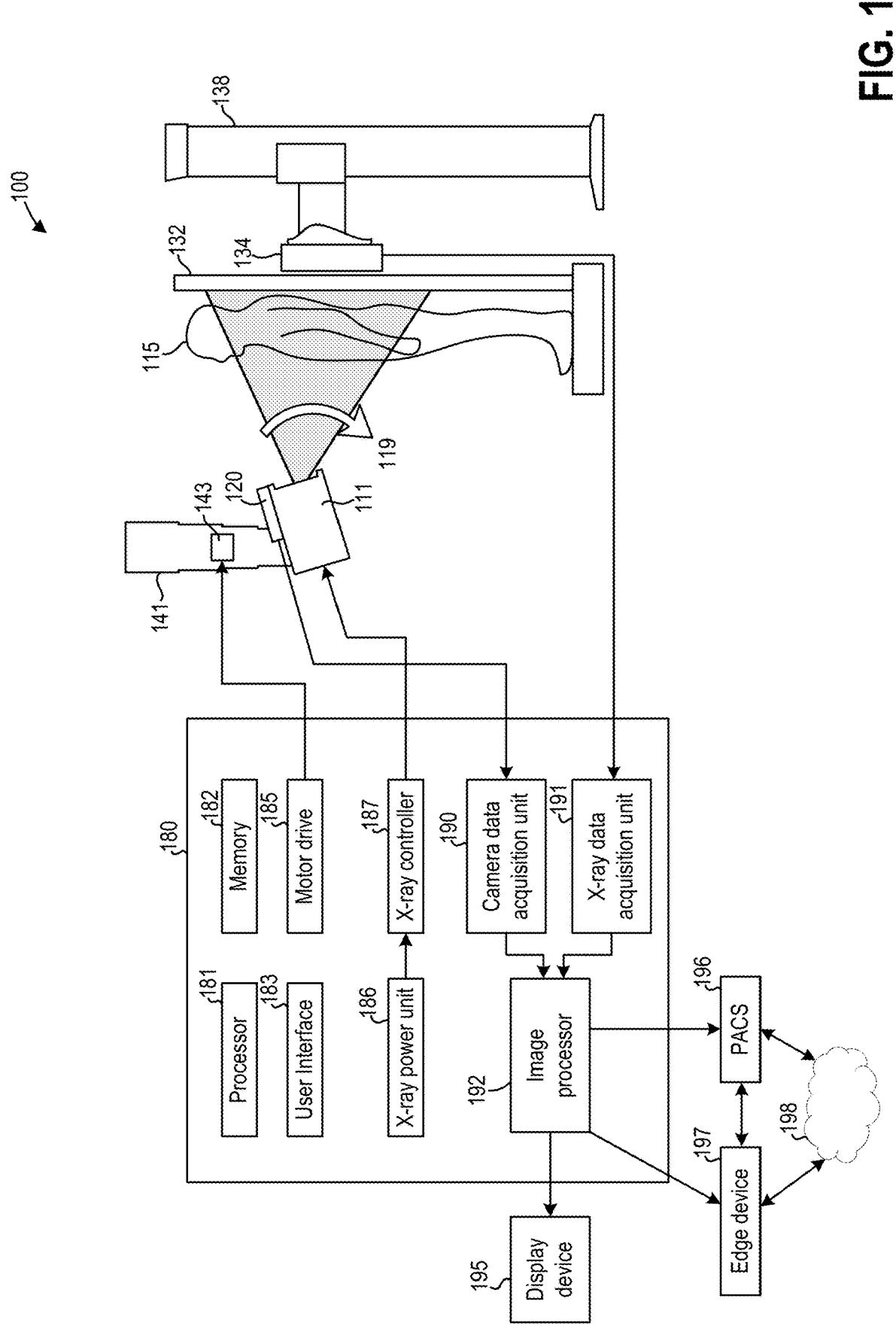
FIG. 1 shows an example x-ray imaging system according to an embodiment.

Clinical development has undergone a transformation in recent years due to the convergence of digital data sources and the efficient use of artificial intelligence (AI) as well as machine-learning models to identify clinically meaningful patterns in data. AI programs have been developed and applied to practices such as diagnosis processes, protocol development, drug development, personalized medicine, and patient monitoring/care. For example, AI can learn features from a large volume of healthcare data, and then use the obtained insights to assist clinical practices in treatment design or risk assessment.

More specifically, AI models have demonstrated remarkable progress in radiological image recognition tasks. Historically, radiological medical images have been visually assessed by trained medical professionals for the detection, characterization, and monitoring of diseases. However, as there is a desire for greater efficacy and efficiency in clinical care and AI methods excel at automatically recognizing complex patterns in imaging data, the use of AI in the identification and characterization of radiographic characteristics is becoming increasingly prevalent. For example, lung cancer screening can help identify pulmonary nodules, with early detection being lifesaving in many patients. AI is now routinely used in the automatic identification of these nodules and the subsequent characterization of them as benign or malignant. Similarly, AI has been used to identify and characterize lesions during abdominal/pelvic imaging, colonic polyps from colonoscopy imaging, microcalcifications from mammography imaging, tumors from brain imaging, and so on. As such, a seamlessly integrated AI component within the imaging workflow may increase efficiency, reduce errors, and achieve objectives with minimal manual input by providing trained radiologists with pre-screened images and identified features. Thus, by automating such processes, institutions may decrease time until diagnosis as well as costs and staffing needs typically associated with such tasks.

Commercially deploying clinical AI models into a medical setting requires a very high burden of proof to regulatory bodies for safety and effectiveness clearance. Therefore, AI developers are limited in how often they can retrain and deploy new models, as all modifications must be reviewed and cleared by a regulatory body. Thus, the same approved static model may be applied across a wide range of clinical settings (e.g., critical care units, emergency rooms, primary care). However, it is anticipated that the optimal operating point for the model may vary between settings/institutions due to patient population differences, imaging equipment variation, radiologist practice/preferences, differing sensitivity versus specificity needs, etc., creating a challenge during commercial deployment as not all customers may be pleased with performance based on these distinctions. As such, some static models may include more than one operating point, or threshold, to allow customers to optimize the model by selecting the operating point that best suits their particular needs. For example, in the case of chest x-rays for certain findings (i.e. life threatening), some radiologists may determine all suspicious findings as a positive needing follow-up for patients and, thus, opt to use an operating point with high sensitivity when deploying a static model. Alternatively, other radiologists will call an image positive only if the radiological finding is obvious/evident since a subtle finding may be a false positive and the condition should also have suffering vital signs to require treatment and, thus, may choose to use an operating point with a high level of specificity when deploying a model for x-ray characterization. However, there are currently no methods to help a customer choose which of the model's operating points is optimal for their needs other than using trial and error or in-depth statistical analysis.

Thus, according to embodiments disclosed herein, a method may be deployed to tune a model's operating point to enable desired performance without retraining the model or potentially triggering a new regulatory clearance. For example, a method may be employed to calculate one or more performance metrics of a model for maximum accuracy based on institution preferences/thresholds for image classification (e.g., in the case of testing for lung nodules, an institution may choose to classify all suspicious chest x-ray findings as positive). Once the operation point for maximum accuracy has been determined, the model's operating threshold may be adjusted to best suit/serve the needs an institution's clinical practice.

Figure 2:
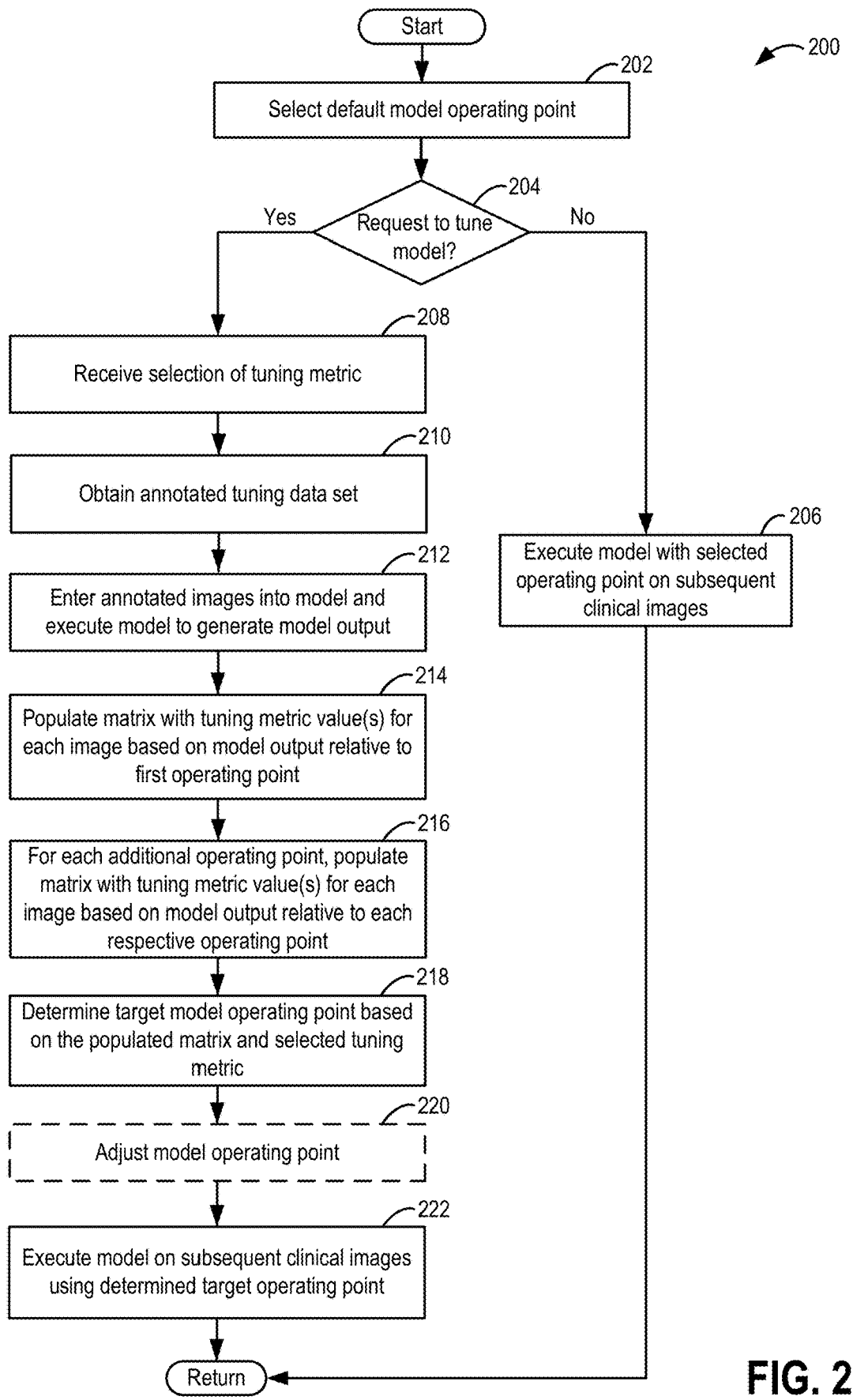
FIG. 2 is a flow chart of a method for tuning a static model.
Figure 3A:
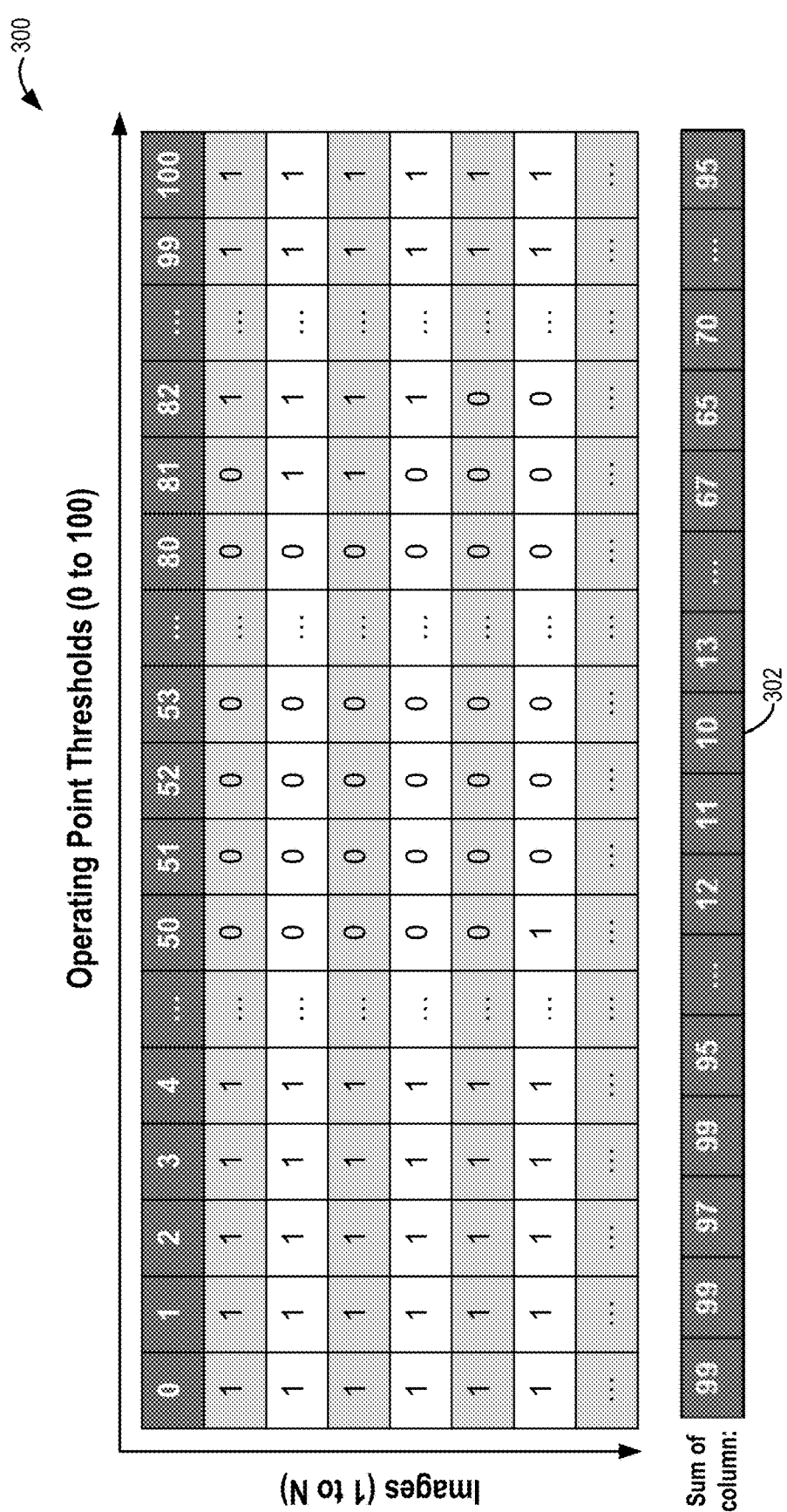
Figure 4:
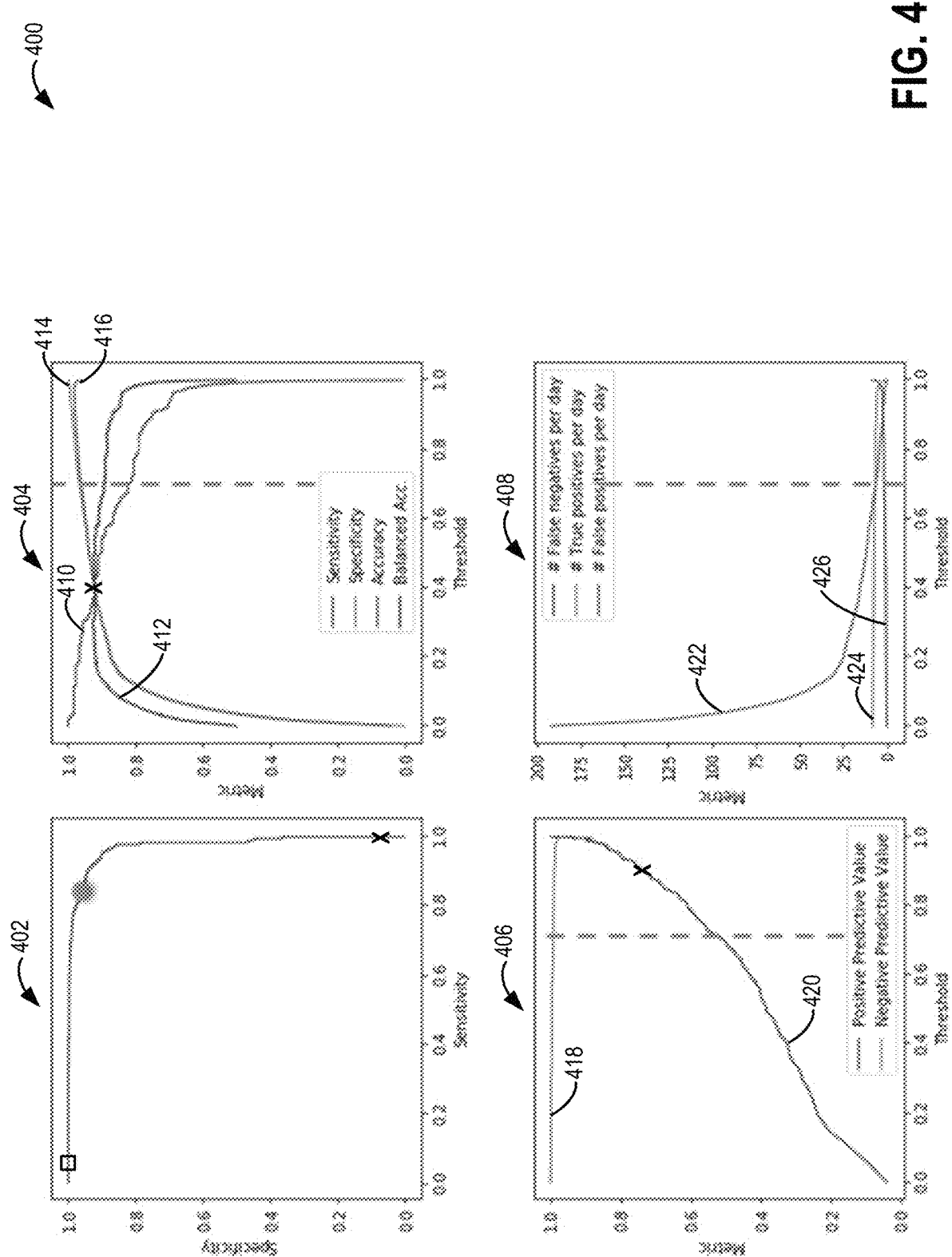
FIG. 4 shows a non-limiting example of graphical data that may be output using the method presented in FIG. 2.
Figure 5A:
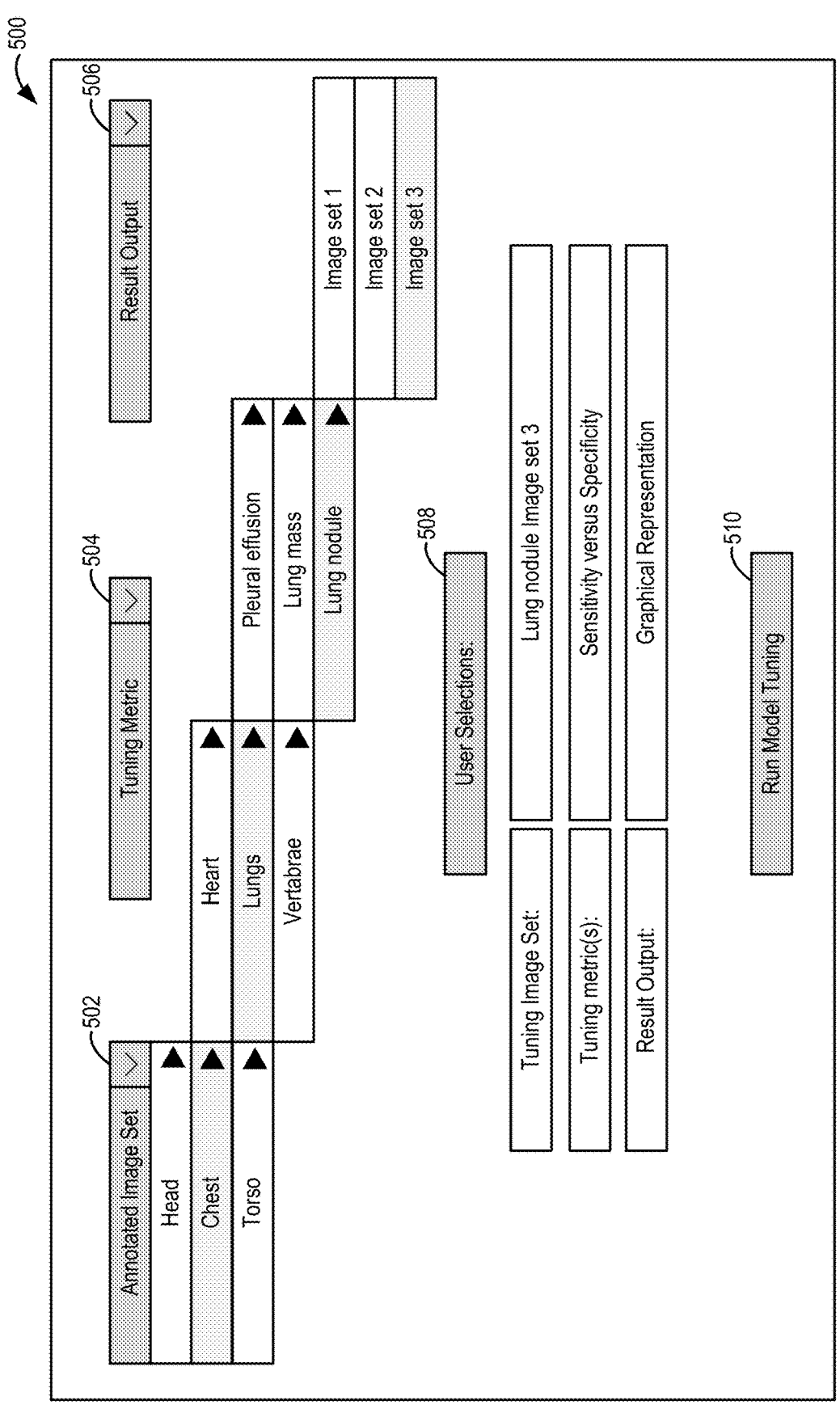
FIGS. 5A and 5B show a non-limiting example graphical user interface that may allow medical staff to tune a static model in a clinical setting.
Figure 5B:
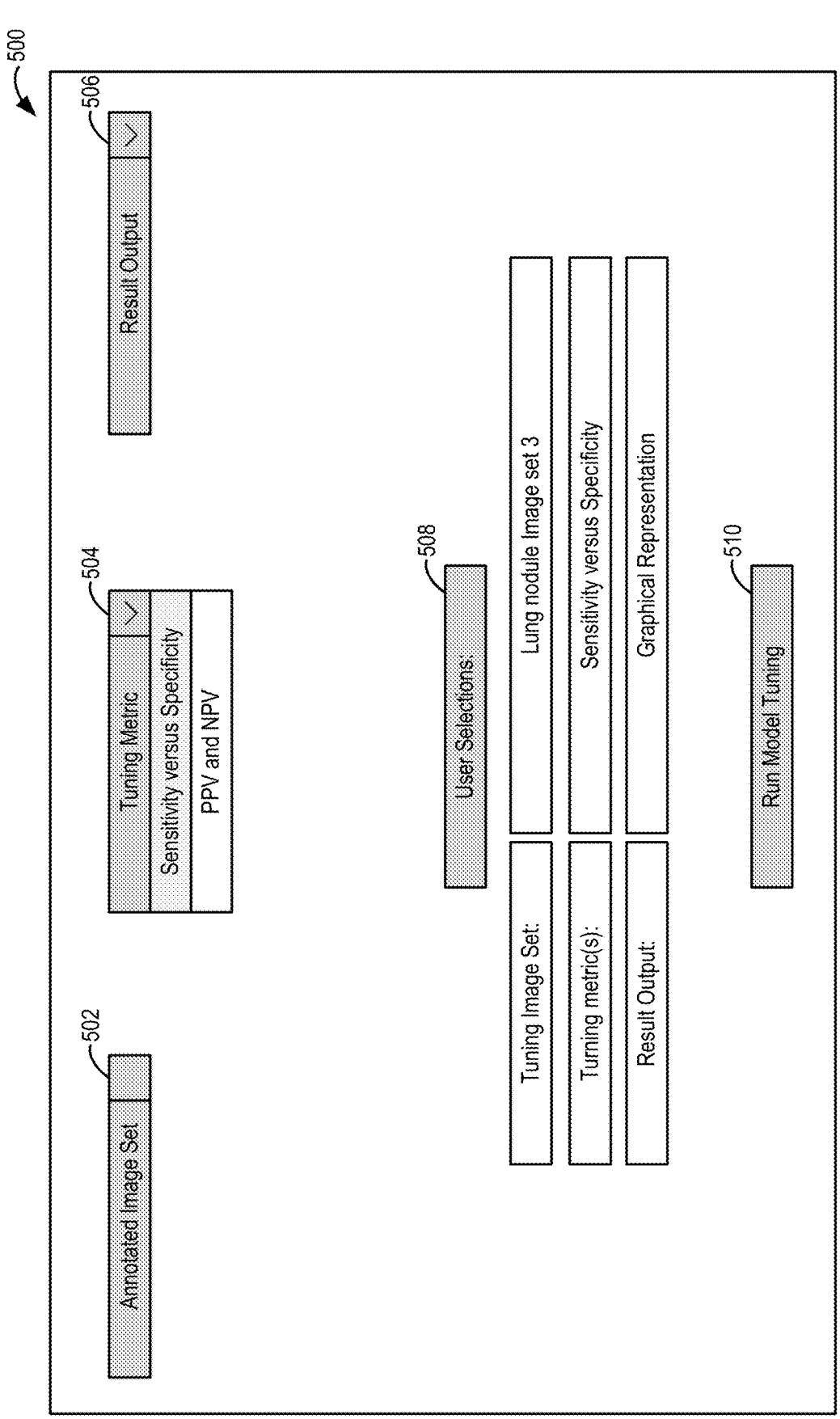
Figure 6:
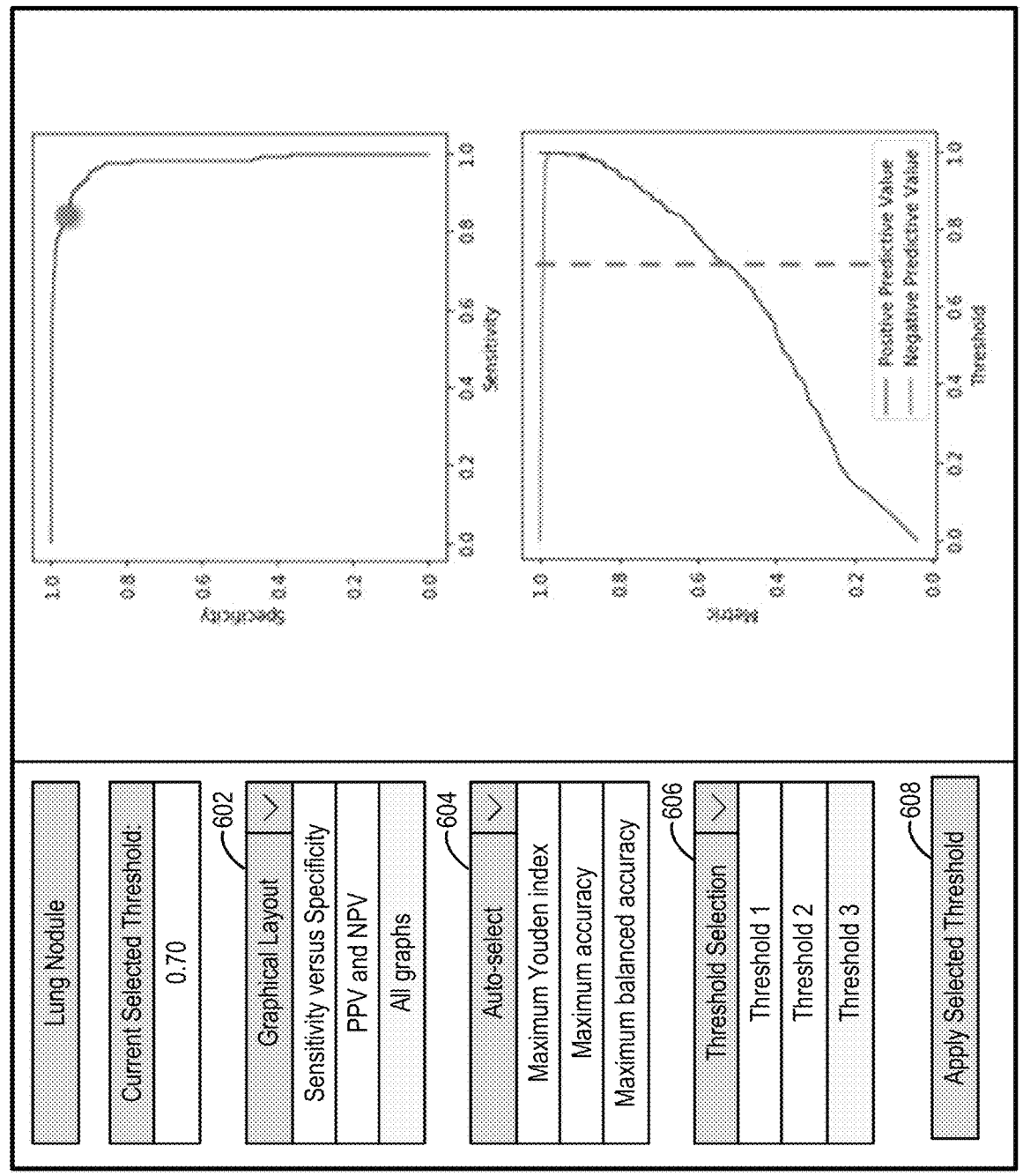
FIG. 6 shows a non-limiting example graphical user interface that may allow medical staff to choose a model operating point for radiological image analysis in a clinical setting.

FIG. 1 depicts an x-ray imaging system that may be used to capture x-ray images that may be employed to tune a static model using the method presented in FIG. 2. FIGS. 3A and 3B show example data matrices of operating point threshold variation that may be generated using the method presented in FIG. 2. FIG. 4 shows an example of graphical data that may be output using the method presented in FIG. 2. FIGS. 5A and 5B show an example graphical user interface (GUI) that may allow medical staff to tune a static model in a clinical setting. FIG. 6 shows an example GUI that may allow medical staff to choose an optimal model operating point for radiological image analysis in a clinical setting. FIGS. 7 and 8 show examples of annotated clinical images that may be part of a tuning dataset used to tune a static model via the method presented in FIG. 2.

Turning now to FIG. 1, a block diagram of an x-ray imaging system 100 in accordance with an embodiment is shown. The x-ray imaging system 100 includes an x-ray source 111 which radiates x-rays, a stand 132 upon which the subject 115 stands during an examination, and an x-ray detector 134 for detecting x-rays radiated by the x-ray source 111 and attenuated by the subject 115. The x-ray detector 134 may comprise, as non-limiting examples, a scintillator, one or more ion chamber(s), a light detector array, an x-ray exposure monitor, an electric substrate, and so on. The x-ray detector 134 is mounted on a stand 138 and is configured so as to be vertically moveable according to an imaged region of the subject.

The operation console 180 comprises a processor 181, a memory 182, a user interface 183, a motor drive 185 for controlling one or more motors 143, an x-ray power unit 186, an x-ray controller 187, a camera data acquisition unit 190, an x-ray data acquisition unit 191, and an image processor 192. X-ray image data transmitted from the x-ray detector 134 is received by the x-ray data acquisition unit 191. The collected x-ray image data are image-processed by the image processor 192. A display device 195 communicatively coupled to the operating console 180 displays an image-processed x-ray image thereon.

The x-ray source 111 is supported by a support post 141 which may be mounted to a ceiling (e.g., as depicted) or mounted on a moveable stand for positioning within an imaging room. The x-ray source 111 is vertically moveable relative to the subject or patient 115. For example, one of the one or more motors 143 may be integrated into the support post 141 and may be configured to adjust a vertical position of the x-ray source 111 by increasing or decreasing the distance of the x-ray source 111 from the ceiling or floor, for example. To that end, the motor drive 185 of the operation console 180 may be communicatively coupled to the one or more motors 143 and configured to control the one or more motors 143.

The x-ray power unit 184 and the x-ray controller 182 supply power of a suitable voltage current to the x-ray source 111. A collimator (not shown) may be fixed to the x-ray source 111 for designating an irradiated field-of-view of an x-ray beam. The x-ray beam radiated from the x-ray source 111 is applied onto the subject via the collimator.

A camera 120 may be positioned adjacent to the x-ray source 111 and may be co-calibrated with the x-ray source 111. The x-ray source 111 and the camera 120 may pivot or rotate relative to the support post 141 in an angular direction 119 to image different portions of the subject 115. The camera 120 may comprise an optical camera that detects electromagnetic radiation in the optical range. Additionally or alternatively, the camera 120 may comprise a depth camera or range imaging camera. As an illustrative and non-limiting example, the camera 120 configured as a depth camera may include an optical camera, an infrared camera, and an infrared projector which projects infrared dots in the field-of-view of the camera 120. The infrared camera images the dots, which in turn may be used to measure depth within the optical camera of the camera 120. As another illustrative and non-limiting example, the camera 120 may comprise a time-of-flight camera. The camera 120 is communicatively coupled to the camera data acquisition unit 190 of the operation console 180. Camera data acquired or generated by the camera 120 may thus be transmitted to the camera data acquisition unit 190, which in turn provides acquired camera image data to the image processor 192 for image processing. For example, as described further herein, the image processor 192 may process the acquired camera images to identify a position of a desired anatomical region for imaging and/or to measure or estimate the thickness of the subject 115 at the desired anatomical region. In some examples, console 180 and/or PACS 196 may include a report module configured to identify and annotate radiological findings in acquired x-ray images (e.g. based on the radiology report using natural language processing (NLP)). Image processor 192 may send processed images to an edge device 197 and/or a picture archiving and communication system (PACS) 196 to which image processor 192 is communicatively coupled. Edge device 197 may be an edge processing device, a cloud processing device, or an extra computing device coupled to a network 198. Further, network 198 may be communicatively coupled with PACS 196 so image data may be transferred between network 198, PACS 196, and/or edge device 197.

Images captured using x-ray imaging system 100 may be subsequently used to tune a static model deployed in automated radiological image recognition tasks. For example, a static model may identify and characterize various radiological findings, such as lesions, microcalcifications, or tumors in x-ray images acquired using a radiological imaging system (such as imaging system 100) and output a positive or negative indication for the finding based on the identification and/or characterization of the findings. The static model implemented in radiological image characterization may output a score (e.g., ranging from 0-100), with a higher score (e.g., closer to 100) more likely indicating a positive finding (e.g., the presence of disease) and a lower score (e.g., closer to 0) more likely indicating a negative finding (e.g., no disease). In some cases, different model thresholds or operating points may be used by the static model in the generation of these scores. For example, the static model may have five operating points corresponding to thresholds of 50%, 70%, 80%, 90%, and 100%, with each threshold impacting a parameter (e.g., sensitivity, specificity) of the model's performance and, thus, impacting the score generated by the model; thereby changing the amount of false and true positives. As such, the model may remain static (e.g., not need to be re-trained and undergo new regulatory clearance) but may be optimized for performance based on the clinical setting/needs of the customer.

Currently, in order for customers to determine which operating point is ideal for their institution, methods involving deep statistical analysis or trial and error may be employed. These tuning methods may be time- and/or resource-intensive, and/or may not result in the model being tuned as optimally as possible. As such, according to the embodiments disclosed herein, a method is provided that may be employed by customers to easily identify which operating point of a static model may best suit their needs based on tuning the model using their own clinical practice data. For example, the method may tune a static model using an image dataset selected from imaging data specific to a given clinical setting (e.g., an institution, a department, unit, or ward, etc.) to determine an optimal operating point for the static model, where the static model is used in the identification and characterization of image findings, patient positioning, and/or proper protocol selection (e.g., a chest protocol is used for imaging a chest). In this way, the operating point of the static model may then be adjusted to optimize performance in the clinical setting.

The systems and methods are described herein with respect to an x-ray imaging system but the methods disclosed herein may be implemented in virtually any other imaging environment without departing from the scope of this disclosure. For example, the methods disclosed herein may be applied to tune a model used to identify findings in images captured via an ultrasound system, magnetic resonance imaging (MRI), computerized tomography (CT) scans, positron emission tomography (PET) scans, single photon emission computed tomography (SPECT) scans, and/or visible light cameras. Further, while the static model is described herein as being stored on and tuned on a specific imaging device (e.g., an x-ray machine), in some examples, the model may be stored and tuned on one or more other devices within an imaging system, such as a PACS (e.g., PACS 196 of x-ray imaging system 100) or another suitable computing device (e.g., edge device 197) communicatively coupled to the imaging system.

FIG. 2 is a flow chart of a method 200 for tuning a static model with multiple operating points to optimize performance within a clinical setting. Method 200 may be executed using computer readable instructions stored in the non-transitory memory of a computing device of an x-ray imaging system or another imaging modality/system located at an institution (e.g., hospital, imaging unit, ward, department), such as memory 182 of FIG. 1. In other examples, method 200 may be executed by another computing device without departing from the scope of this disclosure, such as a PACS (e.g., PACS 196 of FIG. 1) or an edge device (e.g., edge device 197 of FIG. 1).

At 202, a default model operating point for a static model may be selected. The static model may be trained to identify and/or characterize one or more suitable image parameters of clinical images, such as diagnostic findings (e.g., the presence of absence of lung nodules), patient positioning, exposure, image noise/artifacts, proper protocol selection, etc. The default model operating point may be a commercially set operating point or a default operating point previously determined via tuning according to a previous iteration of method 200. Some static models may have only a few predefined possible operating points (e.g., 50, 60, 70, 80, 90) but the selected operating point may be different than the predefined operating points (e.g., the tuning process described herein may be carried out with 100 different operating points). Thus, in some examples, the predefined operating point closest to the operating point selected after tuning may be selected (e.g., if the tuning process identifies 59 as the optimal operating point, the selected operating point may be the closest predefined operating point, which in the prior example may be 60). The tuning process may be carried out with only the possible predefined operating points (e.g., 50, 60, 70, 80, 90) or the tuning process may be carried out with a range of additional possible operating points (e.g., 50-100). In one example, the model's operating points may be different thresholds against which output of the model may be compared to determine whether or not a certain image parameter is present in an image, and which affect one or multiple tuning metrics such as sensitivity, specificity, accuracy, positive predictive value (PPV), and/or negative predictive value (NPV). A user such as medical staff may select the model's default operating point using a GUI such as the GUI presented in FIG. 6.

At 204, method 200 includes determining if a request to tune the static model has been received. A user, such as a clinician or other medical staff, may input a request for the model to be tuned using a suitable user input device, e.g., touch input to a graphical user interface (GUI), such as the GUI presented in, and further described with respect to, FIGS. 5A and 5B. If a request to tune the model has not been received, method 200 proceeds to 206, where the model may be executed with the selected default operating point on subsequent clinical images, after which method 200 may return to the start. The subsequent clinical images may be x-ray images obtained by the x-ray imaging system, and the model may be executed to generate output that is compared to the default operating point in order to provide an indication of the parameter the model is trained to identify/characterize.

If a request to tune the model has been received, method 200 proceeds to 208 to receive a selection of a tuning metric. The tuning metric herein may be defined as an umbrella of evaluation criteria by which operating points may be distinguished based on findings from binary output. Tuning metrics may include sensitivity, specificity, accuracy, balanced accuracy, positive predictive value (PPV), negative predictive value (NPV), and/or the number of false positives/false negatives/true positives/true negatives per day in the institution. The user may request the model be tuned based on clinical setting, the specific patient/patient population, imaging equipment variation, and/or radiologist practice/preferences. For example, the default operating point selected at 202 may be set to identify and characterize radiological findings with a high degree of specificity to decrease potential false alarms during automated identification (e.g., the identification of plural effusions from chest x-rays). While a high degree of specificity may be advantageous in certain clinical settings such as in an intensive care unit (ICU) in which patients are continuously monitored, in other settings staff may prefer the model to operate with a higher degree of sensitivity than specificity (e.g., in settings where the patient is released within the same day as being admitted). For example, a higher degree of sensitivity may be more advantageous than specificity when the model is deployed in emergency rooms (ERs) as potential mischaracterization of a radiological artifact may be life-threatening or contagious. As a non-limiting example, a patient may enter a clinic with tuberculosis. If a model is deployed with an operating point having high degree of specificity, the model may not identify tuberculosis in the chest x-ray of said patient and the patient may be released. In contrast, the same model using an operating point tuned for sensitivity may identify the same chest x-ray as positive for tuberculosis.

At 210, an annotated tuning dataset may be obtained. The annotated tuning dataset may be representative of the institution and may include image data (e.g., x-ray images) annotated by one or more experts at the institution and/or according to institutional preferences to set the model's performance to align with preferences of the institution and/or a sub-group within the institution (e.g., department, ward, etc.). For example, the tuning dataset may be annotated by a selected radiologist who has been trained to indicate an image parameter (e.g., a specific diagnostic finding) according to institutional regulations and preferences, which in some examples may include ward or unit-based preferences (e.g., annotated for a high specificity threshold for patients within an ICU, annotated for a high sensitivity threshold for patients within the ER, annotated for a high sensitivity in a patient population particularly susceptible to a certain disease). In some examples, the tuning dataset may be representative of a specific patient population that is likely to be imaged at the institution, due at least in part to the images in the tuning dataset being obtained at the institution, obtained at the same geographical region of the institution, obtained of patients having the same demographic make-up as those typically admitted to/imaged by the institution, etc. For example, if the static model is deployed on a device of a pediatric hospital, the images in the tuning dataset may be images of children. The annotated tuning dataset may be obtained automatically or manually. Automatic collection of image data representative of the clinical practice may be implemented using a Digital Imaging and Communication in Medicine (DICOM) push or pull data interchange protocol in which images are sent to a specified destination on an edge server (e.g., edge device 197 of FIG. 1) or cloud location (e.g., network 198 of FIG. 1). The image data may then be selected from a specified destination and manually annotated by one or more users, or automatically annotated. Automatic annotation may use NLP on radiology reports to annotate the selected image data, at least in some examples.

In some examples, representative image data for the tuning dataset may be manually selected from clinical images stored on the network or PACS communicatively coupled to the imaging system (e.g., network 198 or PACS 196 of imaging system 100 of FIG. 1) by an expert (e.g., radiologist) who subsequently manually annotates the selected images. In another example, manual image annotation may be implemented by displaying the model's results (explained in more detail below) to a user on a user interface of the imaging system (e.g., user interface 183 of imaging system 100 of FIG. 1) or a web application communicatively coupled to the network or PACS linked to the imaging system. The user may then annotate the image with a finding of being in agreement with the displayed result or a finding of being in disagreement with the displayed result. For example, a displayed clinical image may be labelled with the model's result and include a hand icon with its thumb up as well as a second hand icon with its thumb down. If the user does not agree with the model's characterization/result of the image parameter(s) (e.g., radiological finding) presented, the user may select the icon with the thumb down thereby annotating the image. Alternatively, if the user does agree with the model's result, the user may select the icon with the thumb up to annotate the image as being a correct finding.

In an embodiment, the tuning dataset may be obtained when tuning is requested at 204. In another embodiment, the tuning dataset may be obtained in advance and stored in memory of the computing device, and then reused when tuning is requested at 204. In some examples, the tuning dataset may be continuously collected during clinical usage.

At 212, the annotated images may be entered into the model and the model executed to generate model output. The model output may include, for each image of the tuning dataset that entered into the model, a value that reflects a likelihood that the image has the image parameter(s) the model is trained to identify. For example, if the model is trained to determine if a finding of lung nodules is present in images, the model output may include a value (e.g., from 0-100, 0-10, etc.) that indicates a likelihood that the image includes a finding of lung nodules, with higher values indicating a higher likelihood.

At 214, a matrix is populated with tuning metric value(s) for each image based on the model output relative to a first operating point. The first operating point may be the default operating point selected at 202, a randomly selected operating point (e.g., randomly selected from the set of operating points discussed above), a lowest or highest value operating point of the set of operating points, or the first operating point may be an operating point selected by the user (e.g., if the model has five operating points, the user may select any of these five operating points).

In one embodiment, the matrix may be populated with values determined by directly comparing the model output to the annotation using a binary system. True positive (TP) and true negative (TN) findings within the tuning dataset (e.g., a finding of lung nodules when lung nodules are present, a finding of no lung nodules when no lung nodules are present) and the model output may be labelled as 0 whereas false positive (FP) and false negative (FN) findings within the tuning dataset and the model output (e.g., a finding of lung nodules when no lung nodules are present, a finding of no lung nodules when lung nodules are present) may be labelled as 1. In some embodiments, the values of for the TPs/TNs and FPs/FNs may be reversed (e.g., TPs and TNs may be labelled as 1, FPs and FNs may be labelled as 0). The matrix may be comprised of rows corresponding to the number of images in the tuning dataset and columns corresponding to the different operating points of the model (see the example matrix presented in FIG. 3A for further detail). In some examples, such as when the tuning metric is maximum accuracy, the matrix may be populated with a tuning metric error value for each image at the first operating point by determining the absolute value of the model output finding (labelled as a 1 or 0) minus the annotation finding (labelled as a 1 or 0). For example, if both the model and the expert determine an image as being a TP or TN for a finding, a value of 0 will be entered into the matrix as |1−1|=0. Alternatively, if the model output is different than the annotation (e.g., a FP or a FN), a value of 1 will be generated within the matrix as |1−0|=1 and |0−1|=1.

In some examples, the matrix may be populated with multiple values for each image, such as a value (or character) indicating if the image was a TP, a TN, a FP, or a FN. The number of TPs, TNs, FPs, and FNs for each operating point in a populated matrix may then be used in conjunction with the number of patients assessed for a disease per day and an occurrence rate of the disease in the given patient population to determine other metrics such as the NPV, PPV, sensitivity, specificity, accuracy, balanced accuracy, the Youden index (e.g., the sum of the sensitivity plus the specificity minus one), and/or the number of false positives/false negatives/true positives/true negatives per day in the institution. For example, the number of true positives per day in the institution may be determined by multiplying the number of patients assessed for disease per day by the prevalence of disease and the sensitivity. In another example, the number of false positives per day in the institution may be equal to: the number of patients assessed for disease per day*(1−the prevalence of disease)*(1−specificity). In another example, the number of false negatives per day in the institution may be equal to: the number of patients assessed for disease per day*(the prevalence of disease)*(1−sensitivity). These additional metrics may provide additional help to the user when evaluating the impact of the given operating point to the institution. An example matrix summarizing TPs, TNs, FPs, and FNs for a plurality of images at a plurality of different operating points is shown in FIG. 3B and explained in more detail below.

At 216, for each additional operating point of the set of operating points, the matrix is populated with respective tuning metric values for each image based on the model output relative to each respective operating point. For example, the model output for each image may be compared to a second operating point to determine a positive or negative finding, and the tuning metric value for each image for the second operating point may be determined by comparing the positive or negative finding to the finding of the corresponding annotated image, similar to the determination of the tuning metric values for the first operating point.

At 218, a target model operating point may be determined based on the populated matrix and the selected tuning metric. For example, if the selected tuning metric is maximum accuracy, the tuning metric values in each respective column may be summed. As each column represents performance at one operating point, the column with the lowest sum represents the target operating point for the tuning dataset as it has the least amount of error compared to the expert annotations. If multiple operating points share the same minimum error (e.g., the same total column sum), various methods may be implemented to further differentiate which operating point may be optimal for the customer (e.g., the median operating point may be selected, or the multiple operating points may be tuned for a second parameter).

The target operating point may be selected according to different methods based on which tuning metric is selected. In one embodiment, a metric curve may be determined based on the populated matrix, and a target operating point may be selected using the metric curve and the selected tuning metric, such as sensitivity, specificity, accuracy, PPV, and/or NPV (see FIG. 4 for example metric curves). The target operating point may be selected based on maximum accuracy, maximum Youden index, curve proximity to the upper left corner, etc. Alternatively, a user may be provided with graphs that represent performance metrics along the metric curve or data summations generated from metric curves and the user may select a target operating point that tailors the model's performance to their desired metric. Further, in addition to adapting the operating point to a specific clinical setting/user/users, method 200 may also recalibrate the p value based on the acquired data—either to reflect probability or to reflect rank. The p value may be recalibrated via Platt scaling, a calibration tree, isotonic regression, or another suitable method.

At 220, method 200 optionally includes adjusting the operating point of the model. For example, the target model operating point identified at 218 may be presented to a user via a user interface and the user may select to adjust the operating point to the target operating point, or the user may choose not to adjust the operating point and maintain the default model operating point selected at 202. The selected operating point may then be saved in the memory of the computing device of the imaging system or memory of the computing device communicatively coupled to the imaging system. In some examples, the operating point may be automatically adjusted and saved if the target operating point is different than the default operating point. At 222, the model may be executed on subsequent clinical images (e.g., x-ray images) using the determined target operating point, when indicated (e.g., in response to a user request to execute the model and/or in response to reception of a clinical image that is to be entered as input to the model). For example, a clinical image may be entered into the model as input, the model may output a value indicating a likelihood that the clinical image has a specific image parameter (such as a finding of lung nodules), and the model output may be compared to the target operating point to determine if the clinical image has the image parameter. As a non-limiting example, the model may be trained to detect lung nodules, and may output a likelihood value of 8 when a first clinical image is input into the model. If the target operating point is 7, the first clinical image may be determined to have a positive finding of lung nodules. If the target operating point is 9, the first clinical image may be determined to have a negative finding of lung nodules. In this way, the interpretation of the model output may be adjusted based on tuned operating point, which may affect whether or not specific parameters are identified, without adjusting the static model itself. Method 200 may then return to the start.

FIG. 3A shows a non-limiting example of a matrix 300 populated with a plurality of tuning metric error values that may be generated using method 200. As previously described, each row of the matrix 300 corresponds to one image of an annotated tuning dataset with the number of rows determined by the number of images comprising the tuning dataset (e.g., a tuning dataset comprised of 100 images would generate a matrix with 100 rows, a tuning dataset comprised of 200 images would generate a matrix with 200 rows). Each column of the matrix corresponds to a different operating point (e.g., as shown, the operating points are thresholds). Matrix 300 is comprised of 100 columns and was thus generated using a static model that has 100 different operating points. In other examples, a matrix generated using method 200 may have as few as two columns (e.g., generated from a model that has two operating points) but less than 100 columns or may have more than 100 columns. Populated data within the matrix (shown as 0s and 1s) correspond to whether the model output matches a corresponding annotation for each image in an annotated tuning dataset. A designation of 1 indicates the model output did not match the corresponding annotation as a positive or negative finding whereas a designation of 0 indicates the model output matches the corresponding annotation as a positive or negative finding. Thus, by summing each column, an overall tuning metric error for each operating point may be determined. The operating point representing the column with the lowest sum may then be determined as an optimal operating point for maximum accuracy, as the model output relative to that operating point most closely matches the annotations within the tuning dataset. For example, the sum 302 of column 53 in matrix 300 is ten, which is the lowest overall error of the matrix. Thus, out of comparing 1 to N images of a tuning dataset with the model output, output from operating point 53 did not match ten image annotations. By comparison, operating points one, two, and four did not match the annotations of 99 images within the tuning dataset. Thus, operating point 53 (e.g., a threshold of 53) may be determined as the optimal operating point for the given tuning dataset.

FIG. 3B shows another example matrix 350 which may be generated according to method 200. Matrix 350 may be populated based on comparing model output for a plurality of images to a plurality of operating points to generate model findings, and then comparing the model findings to expert findings for each image of the plurality of images. In contrast to matrix 300, matrix 350 may represent a sum of a larger matrix or plurality of matrices. Matrix 350 includes a plurality of columns, with each column representing an operating point. As shown in FIG. 3B, matrix 350 includes columns for operating points (e.g., thresholds) of 10, 20, 30, 40, 80, 90, and 99, though other operating points are within the scope of this disclosure. For visual purposes, select operating points (e.g., 50, 60, and 70) have been left off of matrix 350.

For each operating point, matrix 350 includes a summation of a plurality of tuning metric values, where each summation indicates how many images from a tuning dataset were determined to have that tuning metric value. For example, matrix 350 includes, for each operating point, the number of images determined to be true positives, false positives, true negatives, and false negatives, as described above with respect to FIG. 2. Based on the tuning metric values for each operating point, various overall tuning metrics may be calculated. As shown, the overall tuning metrics calculated from matrix 350 include sensitivity, specificity, PPV, NPV, accuracy, and balanced accuracy.

Using a static model trained to detect lung nodules as an example, if the static model is tuned to operate with a relatively low operating point (e.g., an operating point of 10), nearly all instances of lung nodules may be detected (e.g., a sensitivity of 97.8%). However, this low operating point may result in a relatively high number of images that do not have lung nodules being classified as having lung nodules (e.g., a specificity of 58.1%). By increasing the operating point, the number of false positives may be reduced (e.g., an operating point of 90 may result in only 17 false positives, compared to 104 false positives for an operating point of 10), but correspondingly the number of false negatives may increase (e.g., from 4 to 44). Thus, the user may select which operating point provides the best balance of sensitivity, specificity, accuracy, etc., for the needs of the specific institution/department.

FIG. 4 shows non-limiting examples of metric curves 400 that may be generated using method 200 to calculate different performance metrics of model operating points. For example, a first metric curve 402 illustrates thresholds for sensitivity and specificity based on data from a populated matrix with tuning metric error for each operating point of the model (e.g., matrix 300 of FIG. 3A). A second set of metric curves 404 generated from a populated matrix illustrates thresholds for sensitivity, specificity, accuracy, and balanced accuracy. A third set of metric curves 406 generated from a populated matrix illustrates thresholds for PPV and NPV. A fourth set of metric curves 408 generated from a populated matrix illustrates thresholds for false negatives, true positives, and false positives. As an optimal operating point may be a compromise between conflicting needs (e.g., sensitivity and specificity), multiple performance metrics may be simultaneously assessed before selecting an operating point. Thus, in one example, a potential user interface (e.g., a GUI such as the GUI presented in FIG. 6) may show all the graphs presented in FIG. 4 to a user at the same time (e.g., all four graphs may be presented on a single screen) so that the user may consider all implications of using a selected operating point.

In another example, the user may use the data presented in the second set of metric curves 404, the third set of metric curves 406, and the fourth set of metric curves 408 as a basis for selecting an optimal operating point. A currently selected operating point (e.g., 0.70) is shown on each set of metric curves, which may enable the user to evaluate all the different metrics for the selected operating point and confirm that the metrics are acceptable. For example, the point on the metric curve 402 may represent the currently-selected operating point, and the dashed line on each of the remaining sets of metric curves may represent the same, currently selected operating point. The user may adjust the operating point by selecting different points on the metric curve 402, or via another form of user input, as explained below. In some examples, the user may select an operating point threshold directly from a displayed graph via input through a mouse (e.g., by clicking on the graph) communicatively coupled to a user interface. In some examples, the user interface may be a touchscreen and the user may touch a threshold on a graph to select a different operating point. In some examples, the user may adjust the threshold up or down using arrow keys on a keyboard communicatively coupled to the user interface. In some examples, an operating point may be automatically selected based on user defined criteria (e.g., the Youden index, maximum balanced accuracy), with the selection appearing on the graphical output so that the user may confirm the selected operating point before use in image analysis.

Metric curve 402 may be generated by plotting a true positive rate (TPR), referred to herein as sensitivity, against a false positive rate (FPR), referred to herein as one minus specificity (e.g., FPR=1−specificity) for each tested operating point. The sensitivity is the ratio of correctly identified positives among all actual positives (e.g., the percentage of actual positive images that were correctly indicated by the model as having a positive finding), while the specificity may be defined as the actual negatives that are correctly identified as negative (e.g., the percentage of actual negative images that were correctly indicated by the model as having a negative finding). Metric curve 402 may be used to automatically select an optimal operating point as previously described. Alternatively, generated metric curves may be output to a GUI (such as the GUI presented in FIG. 6) on a display device so that a user may select an optimal operating point based on the data provided. For instance, a user in a primary care setting may want the model's performance to be balanced between specificity and sensitivity. Thus, if first metric curve 402 was displayed, the user might select an operating point in the middle of the curve for optimal performance (e.g., the operating point represented by the dot on the curve of metric curve 402). Alternatively, if the user works in an ER, he/she may want to select an operating point with a higher level of sensitivity (e.g., the operating point represented by the X on the curve of metric curve 402) as false negatives may be life threatening to patients. On the other hand, a user in an ICU may prefer to minimize false positives as the patients are being continuously monitored and thus the user may select an operating point with high specificity (e.g., the operating point represented by the square on the curve of metric curve 402) for optimal performance.

In the second set of metric curves 404, the third set of metric curves 406, and the fourth set of metric curves 408, the x-axis may represent the operating point (e.g., threshold) of the model yielding the metric value defined by the y-axis. The vertical dashed line within the second set of metric curves 404, the third set of metric curves 406, and the fourth set of metric curves 408 may represent the model's current operating point (e.g., without tuning). The model's current operating point in the second set of metric curves 404, the third set of metric curves 406, and the fourth set of metric curves 408 may be at a threshold of 0.7. For the second set of metric curves 404 and the third set of metric curves 406, the y-axis may represent the determined tuning metric error of each displayed metric normalized to one. Values close to or at zero on the y-axis may correspond to a higher degree of tuning metric error whereas values close to or at one may correspond to a lower degree of or no (e.g., a value of 1) tuning metric error. The y-axis of the fourth set of metric curves 408 may represent the total number of occurrences for each displayed tuning metric (e.g., the total number of false negatives per day).

In some examples, the user may utilize a metric curve to deploy the model with an operating point based on multiple calculated metrics such as sensitivity, specificity, accuracy, and balanced accuracy (e.g., the arithmetic mean of the true positive rate and true negative rate). Thus, if second set of metric curves 404 was displayed, the user may select an operating point based the tuning metric error of a specificity curve 414, a sensitivity curve 410, an accuracy curve 416, and a balanced accuracy curve 412 such as the operating point indicated by the X which correlates to a threshold of 0.4. The 0.4 threshold has a higher degree of sensitivity and balanced accuracy as compared to the model's current operating point threshold of 0.7 (e.g., the dashed vertical line) with a lower degree of accuracy and specificity.

In another example, the user may want to select an operating point based on model tuning for PPV and NPV, with the PPV and NPV of an operating point corresponding to the operating point's degree of precision with regard to the probability of disease within an annotated image. Thus, if the third set of metric curves 406 was displayed, the user may select an operating point based on the tuning metric error of an NPV curve 418 and a PPV curve 420. In the depicted example, the model currently utilizes an operating point with a threshold of 0.7 (e.g., the dashed vertical line) which generates a tuning metric error of about 0.5 which may correlate to about 50% of the model's output matching the tuning datasets annotations of positive findings. Based on model tuning, the user may opt to select a new operating point with a higher or lower degree of tuning metric error as best suited to the user's clinical needs. For example, the user may select an operating point with a higher PPV value, such as a threshold of 0.9 as indicated by the X. Similarly, the user may want to select an operating point based on a false positives per day curve 422, a true positives per day curve 424, and/or a false negatives per day curve based on clinical needs as shown in the fourth set of metric curves 408. After tuning, the user may opt to utilize the model's current operating point (e.g., the dashed vertical line) in which the TPR, FPR, and false negative rate (FNR) are roughly the same, all occurring less than 12 times within a day. Thus, users may optimize the model's performance based on one or more calculated metrics using the method described herein.

FIGS. 5A and 5B show a non-limiting example of a GUI 500 that medical staff may use to tune a static model in a clinical setting according to the method disclosed herein. GUI 500 is comprised of several drop-down menus including an Annotated Image Set menu 502, a Tuning Metric menu 504, and a Result Output menu 506. In other embodiments, GUI 500 may have more or less drop-down menus. For example, a Result Output menu may not be included and the optimal operating point may be automatically determined and applied after tuning using method 200. Once a user has selected various options from the drop-down menus of GUI 500, their selections are displayed under a User Selections banner 508.

To choose a specific annotated tuning dataset, the user may select an annotated image set menu to view a list of body parts/sections. The user may select the body part/section that corresponds to the area that the user would like to image. Once a body part/section has been selected, a second drop-down list may be viewed comprised of anatomical features (e.g., organs and bones) in that body part/section that may be assessed by radiological imaging. Selection of a specific anatomical feature may generate a third drop-down menu comprised of different diseases or radiological findings that may be identified and characterized using the static model. Once a disease or finding has been selected, a fourth drop-down list of annotated image sets may be viewed and an image set selected based on user preference to tune the static model using method 200. For example, as shown in FIG. 5A, a user of GUI 500 has chosen to use Image set 3 to tune to the AI model before imaging the lungs to determine if a patient has lung nodules. In another example, an annotated image set menu may be comprised of one drop-down list of image sets, with each image set labelled according to customer preferences. For instance, image sets may be labelled with disease names and the degree of the parameter for which the images are annotated (e.g., an image set may be labelled "Lung nodule—high sensitivity," whereas a second image set may be labelled "Lung nodule—high specificity"). Alternatively, an annotated image set menu may be comprised of a drop-down list of user names and each user may create sub-lists as desired (e.g., a first user may choose to organize the image sets as described above, a second user may opt to organize image sets by annotations with a sub-list generated for each disease/finding).

Once an annotated image set has been selected, the user may select a tuning metric menu from which a drop-down list of different tuning metrics may be viewed. For example, as shown in FIG. 5B, a user has selected to tune the static model for sensitivity using a Tuning Metric menu 504. Tuning Metric menu 504 only lists sensitivity versus specificity and PPV & NPV as tuning metric options however, in other examples, a tuning metric menu may include additional metrics (e.g., maximum accuracy, balanced accuracy, false positives, false negatives). In other examples, users may select more than one tuning metric (e.g., sensitivity versus specificity and PPV and NPV may both be selected or the menu may include an option to select all metrics). Users may then use a result output menu to choose how they would like the results of the model tuning displayed. For example, as shown in FIGS. 5A and 5B, a user has used Result Output menu 506 to select that the result output be a graphical representation (e.g., metric curves 400 of FIG. 4). In other examples, the result output may be displayed as a summary table or a combination of summary tables and graphs. Once the user has selected an annotated tuning dataset, a tuning metric, and their desired result output, on the user may select a Run Model Tuning button 510 to begin model tuning. Once the model has been tuned, a second GUI may be output comprised of the result output and allowing for user selection of an optimal operating point for subsequent image analysis as shown in FIG. 6.

FIG. 6 shows a non-limiting example of a GUI 600 that may be output following model tuning. For example, the user of GUI 500 selected to have the result output as a graphical representation as shown by the metric curves on the right hand side of GUI 600. GUI 600 further includes a banner stating what disease/finding the model was tuned for in the upper left corner (e.g., lung nodule), under which the value of the current selected threshold/operating point is displayed (e.g., 0.70). GUI 600 is further comprised of a Graphical Layout menu 602 that lists the different graphical output that may be displayed to the user. For example, the user of GUI 500 may have selected to run model tuning using both sensitivity versus specificity and PPV and NPV as tuning metrics, with the result output as graphical representations. Thus, the user of GUI 600 may view graphical data output for sensitivity versus specificity and/or PPV and NPV by selecting an option listed under the Graphical Layout menu 602. The Graphical Layout menu 602 only lists sensitivity versus specificity, PPV and NPV, and all graphs as graphical output options that may be displayed; however, in other examples, a graphical layout menu may include additional metrics (e.g., maximum accuracy, balanced accuracy, false positives, false negatives).

Further, GUI 600 may include an auto-select menu which may allow the user to have a default operating point automatically selected based on user specified criteria. For example, an Auto-select menu 604 may include the maximum Youden index, maximum accuracy, and maximum balanced accuracy. Thus, if the user selects the maximum Youden index as the criteria by which an operating point may be automatically selected, the operating point with the highest Youden index will be determined and applied for subsequent image analysis. Alternatively, the user may use a threshold selection menu to determine an operating point based on the result output presented in GUI 600. For example, the user may select Threshold 3 from a Threshold Selection menu 606 after determining Threshold 3 as the operating point best suited for image analysis based on the graphical data presented. Once users have selected which threshold or operating point they would like to use based on the result data provided (e.g., auto-selected based on selected criteria or specifically selected), they may select an Apply Selected Threshold button 608 to use said operating point for image analysis.

Figure 7A:
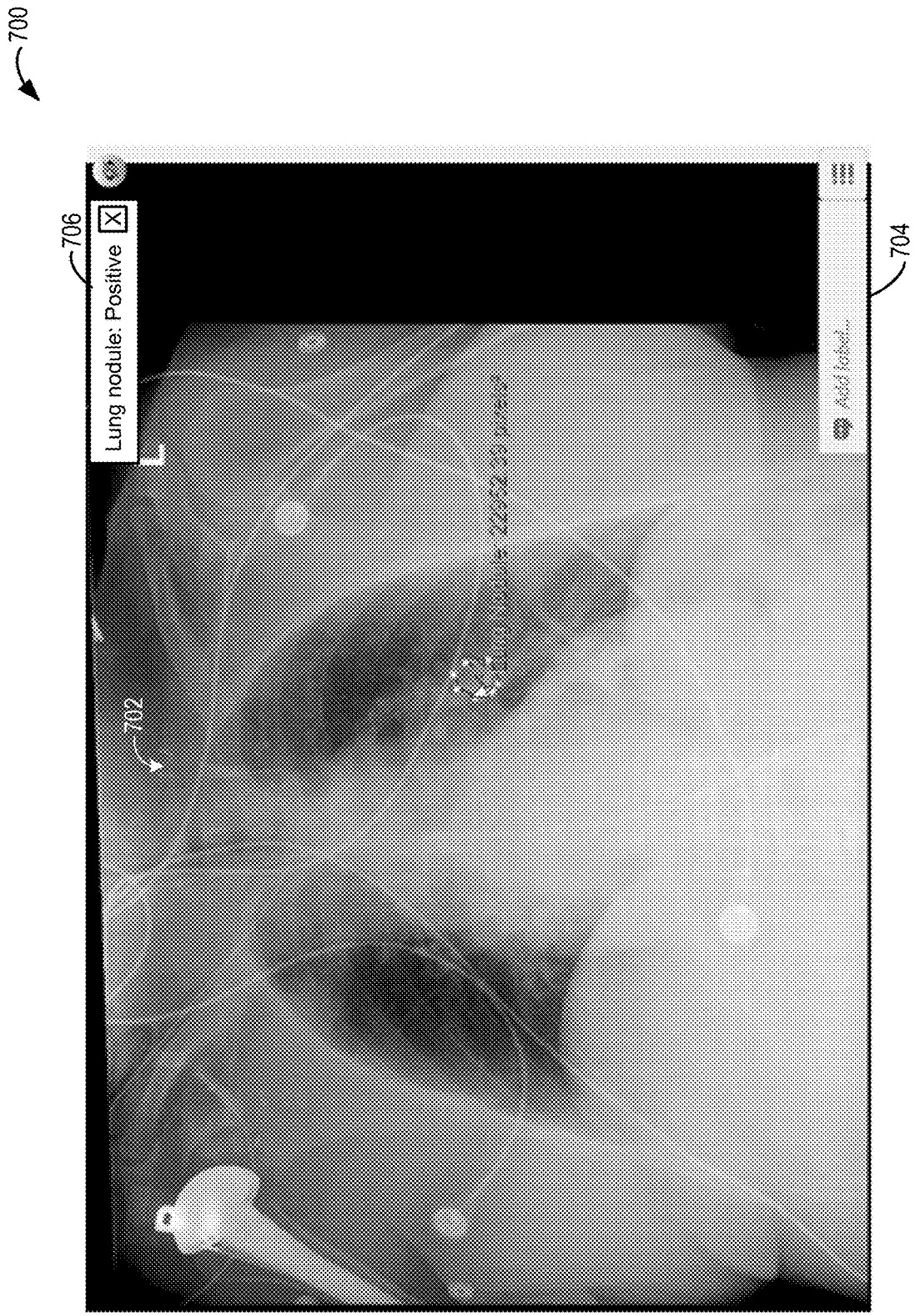
FIGS. 7A and 7B show a non-limiting example of an annotated clinical image that may be part of a tuning dataset used to tune a static model via the method presented in FIG. 2.
Figure 7B:
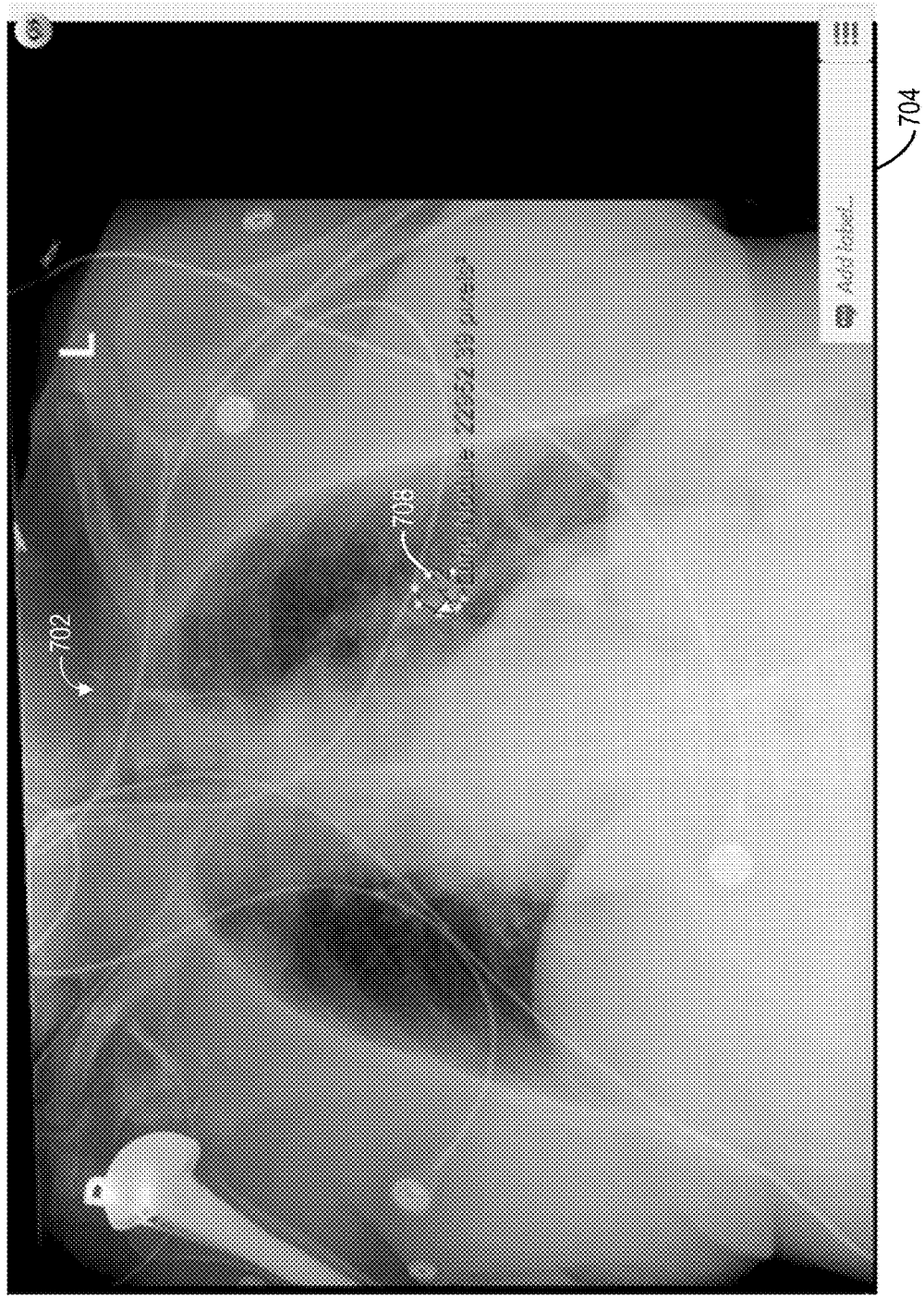

FIGS. 7A and 7B show a non-limiting example of an annotated clinical image 700 that may be part of a tuning dataset used to tune a static model via method 200. An x-ray image 702 may come from an institution's clinical practice data (e.g., obtained by an x-ray machine at the institution) and be annotated by a user (e.g., a radiologist at the institution) via input to text box 704 (e.g., directly typing in the annotation). For example, in FIG. 7A, a user has annotated x-ray image 702 as positive for a lung nodule as shown by annotation label 706. Alternatively, an x-ray image may be annotated using image segmentation. As shown in FIG. 7B, a user has segmented a region of interest (ROI) within x-ray image 702 that corresponds to a positive finding for a lung nodule. Images annotated via segmentation may be used as a tuning dataset to tune a static model via method 200. The operating points of the model may be classified by different thresholds for the transition point between the highest pixel intensity and the lowest pixel intensity forming an edge (e.g., one operating point may determine segmentation on the midpoint of the edge transition, a second operating point may determine segmentation three-fourths of the way through the edge transition, etc.). For example, annotation by segmentation may output an image mask. Each pixel within the image mask may be labelled with a value between 0 and 1, with the value representing the probability the pixel shows disease. The image masks output from the annotated data set may then be used to tune a static model, with a desired operating point determined/selected based on similarity metrics between the image masks and the model output.

In this way, an operating point of a static model may be tuned to enable optimal desired performance according to the method described herein. The embodiments disclosed herein provide a method that may be employed by customers to easily identify which operating point of a static model may best suit their needs based on tuning the model using their own clinical practice data. The technical effect of tuning an operating point of a static model is that performance of the model may be customized to best meet the needs of an institution without retraining the model or potentially triggering a new regulatory clearance.

As used herein, an element or step recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
responsive to a request to tune a pre-trained static model, obtaining a tuning dataset including a set of medical images;
executing the pre-trained static model using the set of medical images as input to generate model tuning output;
determining, for each operating point of a set of operating points, a set of tuning metric values based on the tuning dataset and the model tuning output relative to each operating point;
selecting a tuning metric;
automatically determining a target model operating point based on the selected tuning metric;
selecting an operating point from the set of operating points based on each set of tuning metric values, the set of operating points including the target model operating point that was automatically determined; and upon a request to analyze a subsequent medical image, outputting a representation of a finding output of the pre-trained static model executed at the selected operating point.

2. The method of claim 1, wherein obtaining the tuning dataset including the set of medical images comprises obtaining the set of medical images and a corresponding set of labels, each medical image of the set of medical images associated with a respective label.

3. The method of claim 2, wherein each label indicates a presence or absence of a specific finding and/or a region of interest in the associated medical image.

4. The method of claim 3, wherein the set of operating points includes a set of thresholds, each set of tuning metric values determined by comparing the model tuning output to a different threshold of the set of thresholds.

5. The method of claim 4, wherein determining the set of tuning metric values for each operating point based on the tuning dataset and the model tuning output relative to each operating point comprises, for a first operating point of the set of operating points, determining a respective first tuning metric value for each medical image based on whether an indication of a presence or absence of a specific finding determined based on the model tuning output for that medical image relative to the first operating point matches an indication of a presence or absence of the specific finding of the label corresponding to that medical image.

6. The method of claim 5, wherein selecting the operating point from the set of operating points based on the set of tuning metric values comprises, for each set of tuning metric values, summing the tuning metric values in that set to generate a summary score for each operating point, and selecting the operating point having a summary score that is the closest to a target score.

7. The method of claim 6, wherein outputting the representation of the finding output of the pre-trained static model executed at the selected operating point comprises outputting a notification for display on a display device indicating a presence or absence of the specific finding in the subsequent medical image.

8. The method of claim 1, wherein outputting the representation of the finding output of the pre-trained static model executed at the selected operating point comprises outputting a notification for display on a display device indicating whether or not a patient imaged in the subsequent medical image is positioned at a target position.

9. A system, comprising:
a display device; and
non-transitory memory storing instructions executable by a processor to:
execute a pre-trained static model using a set of medical images of a tuning dataset as input to generate model tuning output;
determine, for each operating point of a set of operating points, a set of tuning metric values based on the tuning dataset and the model tuning output relative to each operating point;
display the set of operating points as options for selection to adjust an operating point, wherein the set of operating points displayed includes an automatically identified target model operating point;
select the operating point from the set of operating points based on each set of tuning metric values; and
upon a request to analyze a subsequent medical image, display on the display device a finding of the subsequent medical image, the finding based on an output of the pre-trained static model relative to the selected operating point.

10. The system of claim 9, wherein the memory and processor are included in an x-ray imaging device, and wherein the subsequent medical image is acquired by the x-ray imaging device.

11. The system of claim 9, wherein the memory and the processor are included in a computing device operably coupled to an imaging device, and wherein the subsequent medical image is acquired with the imaging device.

12. The system of claim 9, wherein selecting the operating point from the set of operating points based on each set of tuning metric values comprises selecting the operating point from the set of operating points based on each set of tuning metric values and further based on a target tuning metric.

13. The system of claim 12, wherein the target turning metric comprises a target sensitivity, a target specificity, a target accuracy, a target positive predictive value, and/or a target negative predictive value.

14. The system of claim 9, wherein the finding of the subsequent medical image is determined by comparing the output of the pre-trained static model to the selected operating point and selecting the finding based on whether the output of the pre-trained static model is greater than the selected operating point.

15. The method of claim 1, wherein analyzing a subsequent medical image occurs without re-training the pre-trained static model itself, and wherein the automatically identified target model operating point is different than the selected operating point.

16. The system of claim 9, wherein the automatically determined target operating point is automatically determined based on a selected tuning metric, and wherein the non-transitory memory further stores instructions executable by the processor to:
receive a user selection of the automatically identified target model operating point from the set of operating points displayed;
adjust the operating point to an adjusted operating point responsive to the user selection of the automatically identified target model operating point; and
analyze the subsequent medical image, and display on the display device another finding of the subsequent medical image based on the output of the static model relative to the adjusted operating point.

17. The method of claim 1, wherein the set of medical images in the tuning dataset is selected from imaging data specific to a specific clinical setting in order to adapt the operating point to the specific clinical setting, and wherein the pre-trained static model is used to identify and characterize at least one of image findings, patient positioning, and proper protocol selection.

18. The method of claim 17, wherein, in addition to adapting the operating point to the specific clinical setting, a p value is further recalibrated.

19. The method of claim 1, wherein the target model operating point is automatically determined using a metric curve in combination with the selected tuning metric.

* * * * *